United States Patent [19]
Short et al.

[11] Patent Number: 5,195,325
[45] Date of Patent: Mar. 23, 1993

[54] LIQUID GAS SAMPLING

[75] Inventors: Frederick J. Short, North Tonawanda; Jeffrey R. Huber, Grand Island, both of N.Y.

[73] Assignee: Praxair Technology, Inc., Danbury, Conn.

[21] Appl. No.: 799,358

[22] Filed: Nov. 27, 1991

[51] Int. Cl.$^5$ ............................................. F17C 9/02
[52] U.S. Cl. ..................................... 62/50.2; 62/37; 62/50.7
[58] Field of Search ................ 62/37, 50.1, 50.2, 50.7

[56] References Cited

U.S. PATENT DOCUMENTS

| | | | |
|---|---|---|---|
| 3,443,028 | 3/1969 | Klee | 62/50.7 |
| 3,726,085 | 4/1973 | Arenson | 62/50.2 |
| 3,972,202 | 8/1976 | Stearns | 62/50.1 |
| 4,715,187 | 12/1987 | Stearns | 62/50.1 |
| 4,773,228 | 9/1988 | Murai et al. | 62/50.1 |

OTHER PUBLICATIONS

Two-Phase Flashing Flow Evaluations, Leung and Nazario, AIChE, Apr. 2, 1989.

HTFS Handbook, TP 10 Single Component Two-Phase Choked Flow, pp. 1-4, 1988.

*Primary Examiner*—Ronald C. Capossela
*Attorney, Agent, or Firm*—Peter Kent

[57] ABSTRACT

Apparatus and method for sampling of a liquified gas for composition analysis. A sample flow of liquified gas is induced into the open end of an admitting tube with sufficient length immersed in the liquified gas to avoid vaporization proximate the open end and in the admitting tube. Joined to the admitting tube is a conveying tube leading to an analyzer. The flow area of the admitting tube is in the range of from about 0.01 to about 0.5 times the the flow area of the conveying tube. In the proximity of the joint is a means for heating the conveying tube so as to vaporize the sample stream. The admitting tube penetrates and extends in a conduit through which, during sampling, liquified gas flows from a vessel containing the liquified gas to be sampled. During nonsampling, the liquified gas flow is valved off and vaporized liquid from the vessel is ducted to the portion of conduit contain in the admitting tube. The vapor enters the open end of the admitting tube and flows through the conveying tube preventing the entry of ambient air and moisture.

18 Claims, 1 Drawing Sheet

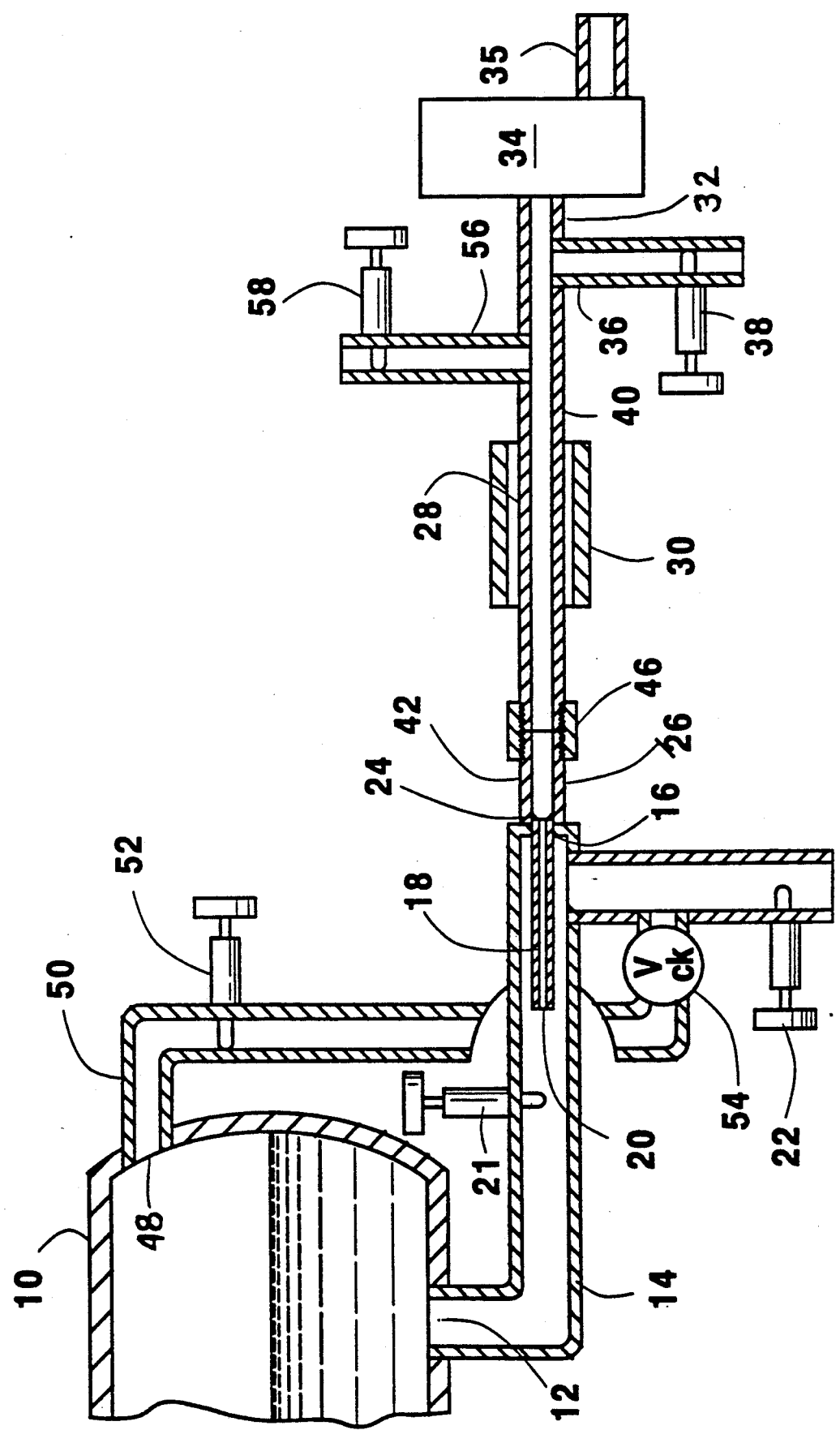

LIQUID GAS SAMPLING

TECHNICAL FIELD

This invention pertains to sampling of liquified gases for composition analysis.

BACKGROUND

Many industrial processes use large quantities of industrial gases, most prevalently the atmospheric gases, which are oxygen, nitrogen, and argon. Commonly, the gases are supplied with not more than 5000 parts per million of impurities or contaminants. Increasingly however, such industrial gases are being required with increasingly higher purity by users. In some new semiconductor manufacturing processes, the gases used must have very low levels of trace contaminants. For example, nitrogen and oxygen are often required with a purity of 99.9999% by volume. The manufacture, storage, transport, distribution and analysis of gases of such high purity has required the development of many new techniques.

Often a gas is manufactured at a site remote from where it is used. When large quantities are required, usually the gas is transported to the use site as a liquid in an insulated truck, stored as a liquid at the use site and vaporized as required for use. Liquified atmospheric gases boil at temperatures well below ambient, are often used as low temperature refrigerants, and hence are known as cryogens. As used herein, liquid cryogen shall mean liquified gas, and vapor cryogen shall mean vaporized liquid cryogen. Cryogens require special handling, transport and storage techniques. The transport of a cryogen in a trailer and transfer from the trailer to a storage tank particularly offer opportunities for contamination of the cryogen.

Thus before liquid cryogen is transferred from a trailer to a storage tank, verification of the purity of the trailer contents is required. In the verification of the purity of liquid nitrogen, for example, analysis is performed for oxygen, moisture, carbon dioxide and total hydrocarbon content. The analyzers used usually accept and analyze a stream of gas. Hence a representative sample stream of liquid cryogen needs to be drawn from the trailer's container, vaporized and delivered to the analyzers, unaltered and uncontaminated.

In the prior art, it has been common to connect a tube of constant diameter from a tap in the bottom of the trailer container to the analyzer, and allow a flow of liquid cryogen to be induced by the pressure difference between the container and the analyzer discharge. Vaporization of the sample stream was accomplished in the sampling tube by natural convection from ambient air, and at times assisted by other heating means.

A number of problems were commonly encountered. One problem was that choked flow would readily occur in the tube owing to the vaporization in the tube. Some of the sample stream then at times would surge or back flow in the sampling tube, thus altering the composition of the sample ultimately reaching the analyzer. Another problem was that in the length of tube where vaporization and hence two phase flow occurred a displacement of the liquid phase from its resultant vapor phase would occur, thus altering the composition of the sample ultimately reaching the analyzer. Still another problem was that low volatility constituents in the cryogen would freeze out and deposit on the walls of the sampling tube, a phenomenon known as plating. This would also alter the composition of the sample stream ultimately reaching the analyzer. Yet another problem was that the sampling process had to be carried out for a long time in order to purge the sampling tube of contaminants which had entered from the atmosphere during its nonuse. Thus the sampling process was wasteful of valuable cryogen as well as unduly long.

The constant diameter tube used in the prior art for drawing a liquid sample was particularly unsatisfactory for an application where an analysis of a liquid cryogen was quickly required, as in analyzing the content of a vessel involved in a process, such as a distillation column in an air separation plant. Such a tube had a long response time, that is, it took a long time for changes in composition in the column to be transmitted in the tube and be reflected at the analyzer.

The prior art also used at times a small, high pressure container to capture a quantity of liquid cryogen which would subsequently be released slowly as a stream, vaporized and delivered to an analyzer. This procedure suffered from the same problems already described, inasmuch as a constant diameter tube was used to purge and supply liquid cryogen from the source to the sample container. Also, it was found that frequently the sample container used was not of sufficient volume to supply a sample stream to adequately purge the discharge line and the analyzer, or group of analyzers in order to obtain an accurate analysis of high purity cryogen.

SUMMARY OF THE INVENTION

The invention provides an apparatus for withdrawing a sample stream of liquid cryogen from a vessel. The apparatus comprises:

(a) an admitting tube having an open end for admitting a stream of liquid cryogen, a joined end, and a length so as to avoid vaporization of liquid cryogen proximate the open end and in the admitting tube when immersed in liquid cryogen;

(b) a conveying tube having one end joined to the admitting tube joined end, the other end capable of connection to a receiver, the internal flow area of the admitting tube being in the range of from about 0.01 to about 0.5 times the internal flow area of the conveying tube; and (c) means for vaporizing the sample stream of liquid cryogen proximate to and downstream of the conveying tube joined end.

In a preferred embodiment, the apparatus further comprises:

(d) a liquid conduit for connection to the vessel, for providing the supply of liquid from the vessel, the admitting tube being mounted in the liquid conduit so that the supply of liquid cryogen is directed around the open end of the admitting tube so as to avoid mixing of liquid at the open end with liquid downstream of the open end;

(e) a first valve in the liquid conduit at a location upstream of the admitting tube;

(f) a second valve in the liquid conduit at a location downstream of the admitting tube;

(g) a vapor conduit for connection to the vessel, for withdrawing a supply of vapor from the vessel, the vapor conduit connecting into the liquid conduit at a location between the first valve and the second valve; and (h) a valve in the vapor conduit.

The invention also provides a method for providing a stream of vaporized liquid sample from a vessel containing liquid and vaporized cryogen, wherein the method comprises the steps of:

(a) providing a supply of liquid cryogen from the vessel;

(b) immersing sufficient length of an admitting tube having a joined end and an open end in the supply of liquid cryogen from the vessel so as to avoid vaporization of liquid cryogen proximate the open end and in the admitting tube;

(c) directing the supply of liquid cryogen around the open end of the admitting tube so as to avoid mixing of liquid at the open end with liquid downstream of the open end;

(d) admitting a stream of liquid cryogen into the open end;

(e) conducting the stream of liquid cryogen from the admitting tube into a conveying tube having one end joined to the admitting tube joined end and the other end capable of connection to a receiver, the internal flow area of the admitting tube being in the range of from about 0.01 to about 0.5 times the internal flow area of the conveying tube;

(f) vaporizing the sample stream of liquid cryogen in the conveying tube proximate to and downstream of the conveying tube joined end; and (g) conveying the vaporized sample stream to a receiver.

Inasmuch as the vessel normally will also contain vapor cryogen, the method preferably further comprises the steps of:

(h) terminating the supply of liquid cryogen from the vessel;

(i) withdrawing a flow of cryogen vapor from the vessel;

(j) directing the flow of cryogen vapor around the open end of the admitting tube so as admit at least a portion of the flow of cryogen vapor into the open end of the admitting tube; and (k) conducting the admitted vapor from the admitting tube into the conveying tube and downstream therefrom so as to prevent entry of air and moisture.

In the application of the method to sampling liquid cryogen from a trailer, the method will preferably further comprise the steps of:

(l) opening a connection in the conveying tube thereby dividing the conveying tube into a trailer section and a site section; and (m) providing a flow of cryogen vapor into said site section so as to prevent entry of air and moisture.

It is another object of this invention that the improved apparatus and method deliver a sample unaltered in composition in a shorter time after activation of the sampling apparatus than prior art apparatus and methods.

It is a feature of this invention that during periods when sampling is not desired, air and moisture are prevented from entering into the apparatus.

It is an advantage of the invention that only a small sample flow and small total quantity of sample are required.

It is another advantage of the invention that it is suitable for continuous analysis as well as intermittent analysis, and for providing a quantity to be captured for subsequent analysis.

It is another advantage that, in continuous analysis applications, the invention provides rapid response to changes in liquid composition at the sampling location.

BRIEF DESCRIPTION OF THE DRAWING

The drawing is a cross sectional representation of a preferred apparatus embodiment of the invention.

DETAILED DESCRIPTION OF THE INVENTION

A preferred apparatus embodiment of the invention is illustrated by way of example in the drawing. A vessel 10 containing cryogenic liquid and vapor has proximate its bottom a lower port 12 communicating with a liquid conduit 14. The vessel 10 is a trailer container, a process vessel, or a storage tank, etc. Near the port 12, the liquid conduit 14 has a penetration 16 for receiving an admitting tube 18 having an open end 20 for admitting a sample stream of liquid cryogen from the conduit 14. The penetration 16 is conveniently at a bend in the conduit 14 so that the admitting tube 18 extends upstream within the conduit 14. During sampling, liquid preferably continuously flows through the first valve 21, through the conduit 14, past the admitting tube 18 and discharges from the conduit 14 through the second valve 22. The flow path is such as to avoid mixing of liquid at the open end 20 of the tube with liquid downstream.

The liquid conduit 14 has a first valve 21 upstream of the admitting tube 18 and a second valve 22 downstream of the admitting tube. Either valve, but preferably the upstream valve 21, is used to prevent liquid from flowing from the vessel 10 through the liquid conduit 14.

At the end of the admitting tube 18 opposite the open end 20 is a joint 24 joining the admitting tube 18 to a conveying tube 26, which has a larger internal area, i.e., flow area, than the admitting tube. The internal area of the admitting tube is in the range of from about 0.01 to about 0.5 times the internal area of the conveying tube, preferably 0.1 to about 0.3 times. A conveying tube with an internal flow area in the range of from about 0.002 to about 1.0 square inches is useable whereas an internal flow area in the range of from about 0.004 to 0.2 square inches is preferred.

The joint between the admitting tube and the conveying tube is located either within or without the liquid conduit, but preferably is close to the penetration in the liquid conduit for receiving the admitting tube. The assembly of the two tubes is mounted in the penetration in the conduit which is sealed to prevent leakage of cryogen. At least sufficient length of admitting tube is immersed in the liquid in the conduit so as to avoid vaporization of liquid cryogen proximate the open end of the admitting tube and in the admitting tube, as by heat conduction from the joint end. Vaporization outside of and proximate the open end of the admitting tube is avoided to avoid the resultant change in the liquid composition and resultant sampling error. Vaporization inside the admitting tube is avoided to avoid choking and to allow sufficient mass flow rate of sample to flow in the admitting tube. Admitting tube lengths in the range of about 0.3 inches to about 100 inches are used, and lengths in the range of about 0.5 to about 10 inches are preferred.

Downstream of and proximate to the joint 24 between the two tubes is a conveying tube section 28 to which is applied a means 30 for heating and vaporizing the sample stream of liquid cryogen carried within the conveying tube. Preferably the means for heating is natural convection from the ambient air. Other means such as an electrical heater are used, particularly if the ambient air is below 32° F. With natural convection, vaporization typically occurs over six to eight feet of conveying tube length.

Opposite the joint end 24 of the conveying tube 26 is a delivery end 32 for connection to a receiver 34, which usually is an analyzer, or group of analyzers in series or parallel, or occasionally a collection tank. An analyzer typically has an outlet 35 for discharging a used sample stream into the atmosphere or a collection duct. Teed into the conveying tube 26 near the delivery end 32 is a bypass or vent line 36 with a control valve 38 to remove any flow in excess of that required for the receiver 34.

In the apparatus embodying this invention, the admitting tube 18 and the conveying tube 26 comprise the sampling line. Since analyzers typically analyze gas samples, all of the liquid admitted into the sampling line is vaporized and delivered as a gas to the analyzers. Typically cryogenic liquids when vaporized and warmed to ambient temperature increase in volume by approximately 700 or 800 times. The sampling line, and particularly the portion of the sampling line carrying vapor, is of appropriate size to induce the desired sample flow with the available pressure drop. Typically the pressure in a liquid cryogen trailer container is a maximum of 30 psig, which therefore, is the available pressure drop for the sampling line and the analyzer in such an application. However, a boost pump can be provided in the sampling line, or a vacuum pump can be provided at the outlet of the receiver in order to provide additional pressure drop to induce greater flow. Since the volume of the sample flow as a liquid is much lower than that as a vapor, in due consideration of the distribution of the pressure drop, the flow area of the portion of the sampling line carrying liquid is much smaller than the flow area of the portion carrying vapor.

Desirably, the sampling apparatus rapidly responds to and transmits to the receiver changes in composition which may occur in the liquid at the admitting end of the admitting tube. Also, waste of cryogen by venting excess sample flow upstream of the receiver is usually avoided. The sampling line usually admits only sufficient sample flow as is necessary for the receiver, vaporizes all of the sample flow admitted, and uses all of the resultant vapor in the receiver.

To achieve these objects, the volume of sample contained in the sampling line, i.e., the holdup, is small. Since liquid when vaporized results in greatly increased volume, the volume of liquid in the sampling line particularly is kept small. This is accomplished by using an admitting tube of small flow area and short length, and vaporizing the sample flow as it leaves the admitting tube and begins to flow in the larger flow area provided by the conveying tube. The larger flow area accommodates the larger volume flow with a reasonable allotment of pressure drop.

The entire sampling line is sized to use the available pressure drop to pass a flow which the receiver will utilize. Typically the available pressure drop is large enough to provide a vapor velocity of from about 4 to about 400 feet per second in the conveying tube, and preferably from about 20 to about 50 feet per second. By providing low residence time for liquid in the sampling line and intense scrubbing on the inside wall of the line, these velocities deter low volatility components in the sample stream, such as water and carbon dioxide, from freezing out and depositing within the sampling line, a phenomenon known as plating.

In an application of the invention to sampling liquid from a trailer, usually the analyzers are permanently mounted at the use site, typically about 100 feet away from a location the trailer can approach. A length of conveying tube 26, denoted as the site section 40, is installed to convey the sample from the trailer to the analyzers. Installed on the trailer is a length of conveying tube, preferably short, denoted as the trailer section 42, for connection to the site section 40. Connecting the trailer section 42 to the site section 40 is a coupling 46.

Normally, the vessel 10 has proximate its top an upper port 48 communicating with a vapor conduit 50 which leads into the liquid conduit 14 at a location between the first valve 21 and the second valve 22 in the liquid conduit 14. The vapor conduit 50 has a block valve 52 and preferably a check valve 54 oriented to prevent flow into the vessel 10. When liquid sampling is not desired, the valves 21 and 22 in the liquid conduit are closed and the valve 52 in the vapor conduit is opened. Vapor from the vessel 10 then replaces the liquid in the liquid conduit 14 and flows around the open end 20 of the admitting tube 18, enters the admitting tube 18, and flows through the sampling line preventing entry of air and moisture into these components.

In application of the sampling apparatus to a trailer, when the coupling 46 in the conveying tube is disassembled to uncouple the trailer, vapor flows from the open coupling end. Also in application of the sampling apparatus to a trailer, the site section 40 of the conveying tube preferably communicates with a site vapor supply conduit 56, which can originate from the top of a site-located storage tank containing liquid and vapor cryogen or compressed vapor alone. When sampling is not desired, a valve 58 in the site vapor supply conduit 56 is opened allowing vapor to flow from the storage tank into the site section 40 of the conveying tube and through the receiver 34 thus preventing entry of air and moisture. When the coupling 46 in the conveying tube is opened to uncouple the trailer, vapor flows through the uncoupled end of the site section of conveying tube thus preventing entry of air and moisture. Each open end of the coupling 46 may then be shielded or connected to a vent line to protect against contamination from the environment.

Thus the sampling line and receiver are kept free of air and moisture when sampling is not in effect. Then when sampling is desired, only a short time is necessary for purging the sampling line with liquid cryogen before an accurate analysis can be performed.

While the present invention has been disclosed in connection with the preferred embodiment thereof, it should be understood that there may be other embodiments which fall within the spirit and scope of the invention as defined by the following claims.

What is claimed is:

1. An apparatus for withdrawing a sample stream of liquid cryogen for analysis, said apparatus comprising:
   (a) an admitting tube having an open end for admitting a stream of liquid cryogen, a joined end, and a length so as to avoid vaporization of liquid cryogen proximate said open end and in said admitting tube when immersed in liquid cryogen;
   (b) a conveying tube having an end joined to said admitting tube joined end and the other end capable of connection to a receiver, the internal flow area of said admitting tube being in the range of from about 0.01 to about 0.5 times the internal flow area of said conveying tube; and (c) means for vaporizing the sample stream of liquid cryogen proximate to and downstream of said conveying tube joined end.

2. The apparatus as in claim 1 wherein the internal flow area of said admitting tube is in the range of from about 0.1 to about 0.3 times the internal area of said conveying tube.

3. The apparatus as in claim 1 wherein the internal flow area of said conveying tube is in the range of about 0.002 to about 1.0 square inches.

4. The apparatus as in claim 1 wherein the internal flow area of said conveying tube is in the range of about 0.004 to about 0.2 square inches.

5. The apparatus as in claim 1 wherein the internal flow area of said conveying tube provides a sample flow velocity of vapor in the range of from about 4 to about 400 feet per second in said conveying tube.

6. The apparatus as in claim 1 wherein the internal flow area of said conveying tube provides a sample flow velocity of vapor in the range of from about 20 to about 50 feet per second in said conveying tube.

7. The apparatus as in claim 1 wherein said admitting tube has a length in the range of from about 0.1 to about 100 inches.

8. The apparatus as in claim 1 wherein said admitting tube has a length in the range of from about 0.5 to about 10 inches.

9. The apparatus as in claim 1 wherein said means for vaporizing the sample stream of liquid cryogen comprises heating by natural convection in ambient air around said conveying tube.

10. The apparatus as in claim 1 further comprising a liquid conduit for providing a supply of liquid cryogen around said admitting tube, said admitting tube mounted in said liquid conduit so that the supply of liquid cryogen is directed around said open end of said admitting tube so as to avoid mixing of liquid at said open end with liquid downstream of said open end.

11. The apparatus as in claim 10 further comprising a first valve in said liquid conduit for preventing liquid from flowing in said conduit.

12. The apparatus as in claim 11 wherein said first valve in said liquid conduit is at a location upstream of said admitting tube, and said apparatus further comprises a second valve in said liquid conduit at a location downstream of said admitting tube.

13. The apparatus as in claim 12 wherein the vessel also contains vapor cryogen and the apparatus further comprises a vapor conduit for connection to and withdrawing a flow of vapor from an external source, said vapor conduit connecting into said liquid conduit at a location between said first valve and said second valve.

14. The apparatus as in claim 1 further comprising a coupling in said conveying tube, said coupling dividing said conveying tube into a trailer section and a site section, the apparatus further comprising a site section vapor conduit entering into said site section, said site section vapor conduit for conveying vapor cryogen from an external source into said site section during periods when analysis is not desired.

15. A method for withdrawing for analysis a sample stream of liquid cryogen, said method comprising:

(a) immersing a length of an admitting tube having a joined end and an open end in a supply of liquid cryogen so as to avoid vaporization of liquid cryogen proximate said open end and in said admitting tube;

(b) admitting a stream of liquid cryogen into said open end;

(c) conducting the stream of liquid cryogen from said admitting tube into a conveying tube having one end joined to said admitting tube joined end and the other end capable of connection to a receiver, the internal flow area of said admitting tube being in the range of from about 0.01 to about 0.5 times the internal flow area of said conveying tube;

(d) vaporizing the sample stream of liquid cryogen in said conveying tube proximate to and downstream of said conveying tube joined end; and (e) conveying the vaporized sample stream to a receiver.

16. The method as in claim 15 further comprising the step of:

(f) directing the supply of liquid cryogen around the open end of the admitting tube so as to avoid mixing of liquid at the open end with liquid downstream of the open end.

17. The method as in claim 16 further comprising the steps of:

(h) terminating the supply of liquid cryogen;

(i) providing a flow of cryogen vapor;

(j) directing the flow of cryogen vapor around the open end of said admitting tube so as to admit at least a portion of the flow of cryogen vapor into said open end of said admitting tube; and (k) conducting the admitted vapor from said admitting tube into said conveying tube and downstream therefrom so as to prevent entry of air and moisture.

18. The method of claim 17 further comprising the steps of:

(l) opening a connection in said conveying tube thereby dividing the conveying tube into a trailer section and a site section;

(m) providing a flow of cryogen vapor into said site section so as to prevent entry of air and moisture.

* * * * *